United States Patent
Inoue et al.

(10) Patent No.: US 9,878,976 B2
(45) Date of Patent: Jan. 30, 2018

(54) METHOD FOR PRODUCING CATIONIC SURFACTANT

(71) Applicant: KAO CORPORATION, Tokyo (JP)

(72) Inventors: Katsuhisa Inoue, Wakayama (JP); Haruka Yoshida, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/510,991

(22) PCT Filed: Oct. 28, 2015

(86) PCT No.: PCT/JP2015/081100
§ 371 (c)(1),
(2) Date: Mar. 13, 2017

(87) PCT Pub. No.: WO2016/080194
PCT Pub. Date: May 26, 2016

(65) Prior Publication Data
US 2017/0275560 A1 Sep. 28, 2017

(30) Foreign Application Priority Data

Nov. 18, 2014 (JP) ................... 2014-233577
Jul. 23, 2015 (JP) ................... 2015-145610

(51) Int. Cl.
| | | |
|---|---|---|
| *C07C 213/06* | (2006.01) | |
| *C11D 1/62* | (2006.01) | |
| *C07C 219/16* | (2006.01) | |
| *C07C 213/10* | (2006.01) | |

(52) U.S. Cl.
CPC .......... *C07C 213/06* (2013.01); *C07C 219/16* (2013.01); *C11D 1/62* (2013.01); *C07C 213/10* (2013.01)

(58) Field of Classification Search
CPC ... C07C 213/06; C07C 213/10; C07C 219/16; C11D 1/62
See application file for complete search history.

(56) References Cited

U.S. PATENT DOCUMENTS

| | | | | |
|---|---|---|---|---|
| 5,670,677 A | * | 9/1997 | Ponsati Obiols | ........ A61K 8/45 554/108 |
| 2002/0002298 A1 | * | 1/2002 | Bigorra Llosas | ..... C07C 213/06 554/114 |

FOREIGN PATENT DOCUMENTS

| | | | | |
|---|---|---|---|---|
| JP | 4-508804 A | | 11/1992 | |
| JP | 8-507756 A | | 8/1996 | |
| WO | WO 2004/060854 | * | 7/2004 | ........... C07C 213/06 |
| WO | WO 2004/060854 A1 | | 7/2004 | |
| WO | WO 2007/131152 A1 | | 11/2007 | |

OTHER PUBLICATIONS

International Search Report for PCT/JP2015/081100 (PCT/ISA/210) dated Feb. 8, 2016.
Written Opinion of the International Searching Authority for PCT/JP2015/081100 (PCT/ISA/237) dated Feb. 8, 2016.

* cited by examiner

*Primary Examiner* — Yate' K Cutliff
(74) *Attorney, Agent, or Firm* — Birch, Stewart, Kolasch & Birch, LLP

(57) ABSTRACT

The present invention provides a method for producing a high quality cationic surfactant, which is prevented from smelling and coloring, and has favorable storage stability. The production method includes the following step 1, step 2, step 3, and step 4:

step 1: a step of obtaining an alkanolamine ester by reacting an alkanolamine with a fatty acid or a fatty acid alkyl ester without using hypophosphoric acid or a salt thereof;

step 2: a step of obtaining a cationic surfactant by quaternizing the alkanolamine ester obtained in the step 1 with a dialkyl sulfate;

step 3: a step of performing an oxidation treatment of the cationic surfactant obtained in the step 2; and step 4: a step of performing a reduction treatment of the cationic surfactant subjected to the oxidation treatment obtained in the step 3.

14 Claims, No Drawings

METHOD FOR PRODUCING CATIONIC SURFACTANT

FIELD OF THE INVENTION

The present invention relates to a method for producing a cationic surfactant, and more particularly relates to a method for producing a cationic surfactant, which has favorable biodegradability, is prevented from smelling and coloring, and has excellent storage stability, and a cationic surfactant produced by the method.

BACKGROUND OF THE INVENTION

Recently, as a cationic surfactant to be used in a fabric softener, in consideration of biodegradability when residues in drainage after a softening treatment are released in nature such as rivers, a cationic surfactant obtained by reacting triethanolamine, methyldiethanolamine, or the like with a long-chain fatty acid or a fatty acid methyl ester, thereby synthesizing an alkanolamine ester as an intermediate, and then, quaternizing the alkanolamine ester with a dialkyl sulfate such as dimethyl sulfate or diethyl sulfate is favorably utilized.

However, such a cationic surfactant having an ester group has a problem that an offensive odor is generated due to a sulfur (S)-containing compound such as methanethiol or dimethyl disulfide produced as a by-product derived from a quaternizing agent used during the production, deterioration of smell or hue due to long-term preservation during storage adversely affects the quality of a commercial product, or the like. With respect to such a problem, JP-A-8-507756 discloses a method in which a peroxide and an alkali metal borohydride are added to the alkanolamine ester before quaternization, and also JP-A-4-506804 discloses a method in which air is brought into contact with the alkanolamine ester before quaternization.

The methods disclosed in the prior art such as JP-A-8-507756 and JP-A-4-506804 are not sufficiently effective in improving the quality with respect to smell and hue after production and during storage. The present invention provides a method for producing a cationic surfactant which is useful as a softening base, has favorable biodegradability, is prevented from smelling and coloring, and has excellent storage stability, and also provides a cationic surfactant produced by the method.

According to the present invention, a method for producing a cationic surfactant including the following step 1, step 2, step 3, and step 4 is provided:

step 1: a step of obtaining an alkanolamine ester by reacting an alkanolamine with a fatty acid or a fatty acid alkyl ester without using hypophosphoric acid or a salt thereof;

step 2: a step of obtaining a cationic surfactant by quaternizing the alkanolamine ester obtained in the step 1 with a dialkyl sulfate;

step 3: a step of performing an oxidation treatment of the cationic surfactant obtained in the step 2; and step 4: a step of performing a reduction treatment of the cationic surfactant subjected to the oxidation treatment obtained in the step 3.

According to the present invention, a high quality cationic surfactant, which is prevented from smelling and coloring and has favorable storage stability, can be obtained by performing an esterification reaction or a transesterification reaction of an alkanolamine thereby obtaining an alkanolamine ester, quaternizing the alkanolamine ester, and then, performing an oxidation treatment and a reduction treatment in this order. The obtained cationic surfactant is useful as a softening base to be used in a fabric softener, and also has favorable biodegradability.

EMBODIMENTS OF THE INVENTION

The step 1 of the invention is a step of obtaining an alkanolamine ester by reacting an alkanolamine with a fatty acid or a fatty acid alkyl ester without using hypophosphoric acid or a salt thereof.

Here, the phrase "without using" hypophosphoric acid or a salt thereof means that hypophosphoric acid or a salt thereof is not used substantially, that is, even if it is used, the using amount thereof is preferably 0.01 parts by mass or less, more preferably 0.005 parts by mass or less, and further preferably 0.001 parts by mass or less with respect to 100 parts by mass of the total amount of the alkanolamine, the fatty acid, and the fatty acid alkyl ester in the step 1 from the viewpoint of reduction of smell. Incidentally, a catalyst other than hypophosphoric acid or a salt thereof can be used within a range that does not impair the effect of the present invention.

The esterification reaction is known to be accelerated by a catalyst such as hypophosphoric acid or an alkali metal salt thereof or an alkaline earth metal salt thereof. Such a catalyst may sometimes adversely affect the smell of a quaternized material by degradation during the reaction. In the step 1 of the present invention, a countermeasure against such an adverse affect is taken by reacting an alkanolamine with a fatty acid or a fatty acid alkyl ester without using hypophosphoric acid or a salt thereof, thereby obtaining an alkanolamine ester. In the step 1 of the present invention, a catalyst other than hypophosphoric acid or a salt thereof can be used within a range that does not impair the effect of the present invention.

The alkanolamine is preferably a dialkanolamine or a trialkanolamine, more preferably an aminoalcohol such as triethanolamine or methyldiethanolamine, and further preferably triethanolamine from the viewpoint of excellent biodegradability and softening performance. The fatty acid to be used for the esterification reaction is a long-chain fatty acid having preferably 8 or more and 30 or less carbon atoms, and more preferably 12 or more and 24 or less carbon atoms such as beef tallow fatty acid, hydrogenated beef tallow fatty acid, palm oil fatty acid, hydrogenated palm oil fatty acid, or a mixture of two or more members selected from these fatty acids from the viewpoint of excellent softening performance. Further, from the viewpoint of excellent softening performance, the fatty acid alkyl ester to be used in the reaction is preferably a lower alkyl ester, more preferably a lower alkyl ester having 1 or more and 3 or less carbon atoms, and further preferably methyl ester of any of these fatty acids.

The esterification degree of the alkanolamine ester, that is, the molar number of the fatty acid bound to the alkanolamine is preferably 1.0 or more, more preferably 1.2 or more, further preferably 1.4 or more, and furthermore preferably 1.6 or more from the viewpoint of excellent blending stability in the softener and excellent softening performance, and is preferably 2.2 or less, more preferably 2.0 or less, further preferably 1.8 or less, and furthermore preferably 1.7 or less from the same viewpoint.

In the step 1, from the viewpoint of improvement of the reaction rate, a carrier gas such as an inert gas may be used depending on the situation, and preferably, nitrogen gas is used.

The reaction temperature in the step 1 is preferably 140° C. or higher, and more preferably 160° C. or higher from the viewpoint of improvement of the reaction rate, and is preferably 230° C. or lower, more preferably 210° C. or lower, and further preferably 200° C. or lower from the viewpoint of prevention of coloration or a side reaction. The reaction pressure in the step 1 is preferably a reduced pressure, more preferably 50 kPa or less, and further preferably 20 kPa or less from the viewpoint of improvement of the reaction rate by removing liberated water, and is preferably 1 kPa or more, and more preferably 5 kPa or more from the viewpoint of burden on production facilities. The reaction in the step 1 is preferably performed by aging at a pressure within the above-mentioned range from the viewpoint of enhancement of the reaction ratio to reduce the amount of the residual starting material fatty acid.

The reaction time in the step 1 is preferably 0.5 hours or more, more preferably 1 hour or more, further preferably 2 hours or more, furthermore preferably 3 hours or more, and yet still further more preferably 6 hours or more from the viewpoint of enhancement of the reaction ratio to reduce the amount of the residual starting material fatty acid, and is preferably 20 hours or less, more preferably 15 hours or less, further preferably 10 hours or less, and furthermore preferably 8 hours or less from the viewpoint of productivity. Further, in the case where the step 1 is performed under reduced pressure, the sum of the time required for reducing the pressure and the reaction time is preferably 1 hour or more, more preferably 2 hours or more, further preferably 3 hours or more, furthermore preferably 4 hours or more, and furthermore preferably 7 hours or more from the viewpoint of enhancement of the reaction ratio to reduce the amount of the residual starting material fatty acid, and is preferably 25 hours or less, more preferably 18 hours or less, further preferably 12 hours or less, and furthermore preferably 9 hours or less from the viewpoint of productivity.

The acid value (mgKOH/g) of the alkanolamine ester obtained in the step 1 is preferably 10 or less, more preferably 6 or less, further preferably 4 or less, furthermore preferably 3 or less, and furthermore preferably 2.5 or less from the viewpoint of prevention of a decrease in the softening performance due to a low reaction rate resulting in leaving the starting material fatty acid. The lower limit of the acid value is not particularly limited, but from the viewpoint of productivity, it may be 0.5 or more, 1.0 or more, 1.5 or more, or 1.7 or more.

In the step 1, from the viewpoint of stabilization of the hue, it is preferred to use a phenolic antioxidant. As the phenolic antioxidant, preferably one or more selected from a bis-alkylhydroxy toluene and a bis-alkylanisole, more preferably one or more selected from 2,6-di-tert-butyl-4-methylphenol (hereinafter, also referred to as "BHT") and 2,6-di-tert-butylanisole, further preferably BHT is used. From the same viewpoint, the using amount of the phenolic antioxidant with respect to 100 parts by mass of the total amount of the alkanolamine, the fatty acid, and the fatty acid alkyl ester is preferably 0.005 parts by mass or more, more preferably 0.01 parts by mass or more, and further preferably 0.03 parts by mass or more, and from the viewpoint of economic efficiency, it is preferably 0.5 parts by mass or less, more preferably 0.1 parts by mass or less, and further preferably 0.07 parts by mass or less.

The step 2 of the present invention is a step of obtaining a cationic surfactant by quaternizing the alkanolamine ester obtained in the step 1 with a dialkyl sulfate.

From the viewpoint of reactivity as the quaternizing agent, economic efficiency, and industrial availability, as the dialkyl sulfate, dimethyl sulfate or diethyl sulfate is preferably used, and dimethyl sulfate is more preferred.

From the viewpoint of prevention of deterioration of the hue and safety such as inflammability, it is preferred to use a carrier gas such as an inert gas in the step 2, and from the viewpoint of economic efficiency, nitrogen gas is preferably used.

The using amount of the dialkyl sulfate with respect to 1 equivalent of the alkanolamine ester is preferably 0.90 equivalents or more, and more preferably 0.93 equivalents or more from the viewpoint of improvement of the quaternization ratio, and is preferably 1.00 equivalent or less, and more preferably 0.98 equivalents or less from the viewpoint of prevention of deterioration of smell or a side reaction.

The quaternization reaction is preferably performed in the absence of solvents from the viewpoint of achievement of a high quaternization ratio. Further, from the viewpoint of reduction of the viscosity to improve the operability during production, an organic solvent can be used. From the viewpoint of the affect of smell on a softener product, industrial availability, economic efficiency, and the like, the organic solvent is preferably at least one organic solvent selected from alcohols having 2 or more and 3 or less carbon atoms and solvents represented by the following general formula (1).

$$R^1\text{—O-(AO)}_n\text{—}R^2 \tag{1}$$

In the formula, $R^1$ and $R^2$ are the same or different and each represent hydrogen, an alkyl group having 1 or more and 30 or less carbon atoms, an alkenyl group having 1 or more and 30 or less carbon atoms, or an acyl group having 1 or more and 30 or less carbon atoms; A represents an alkylene group having 2 or more and 4 or less carbon atoms, and n represents a number on average of 1 or more and 40 or less, and A's are all the same or some of them may be different.

From the same viewpoint, the organic solvent is more preferably a monohydric alcohol having 2 or more and 3 or less carbon atoms or a polyhydric alcohol having 2 or more and 3 or less carbon atoms, and further preferably ethanol or isopropyl alcohol.

The using amount of the organic solvent to be used in the quaternization reaction in the step 2 with respect to 100 parts by mass of the total amount of the alkanolamine ester and the dialkyl sulfate is preferably 0.1 parts by mass or more, more preferably 1 part by mass or more, and further preferably 3 parts by mass or more from the viewpoint of reduction of the viscosity to improve the handleability, and is preferably 15 parts by mass or less, more preferably 12 parts by mass or less, and further preferably 10 parts by mass or less from the viewpoint of improvement of the quaternization ratio.

In the quaternization reaction, from the viewpoint of control of the temperature due to the heat of the reaction and prevention of a local overreaction of the dialkyl sulfate, the reaction is preferably performed while supplying the dialkyl sulfate to the alkanolamine ester.

The supply temperature of the dialkyl sulfate is preferably 30° C. or higher, and more preferably 40° C. or higher from the viewpoint of improvement of the reaction rate, and is preferably 100° C. or lower, more preferably 90° C. or lower, further preferably 80° C. or lower, and furthermore preferably 70° C. or lower from the viewpoint of prevention of deterioration of smell and prevention of a side reaction. Further, the supply time of the dialkyl sulfate is preferably 0.1 hours or more, more preferably 0.25 hours or more, further preferably 0.5 hours or more, and furthermore preferably 1 hour or more from the viewpoint of prevention of a side reaction, and is preferably 20 hours or less, more preferably 10 hours or less, further preferably 5 hours or less, furthermore preferably 4 hours or less, and furthermore preferably 3 hours or less from the viewpoint of productivity.

The quaternization reaction may be performed at normal pressure (0.1 MPa) or may be performed under pressure or under reduced pressure. The reaction pressure (in absolute pressure) is preferably 0.09 MPa or more, and more preferably 0.10 MPa or more, and is preferably 0.5 MPa or less, more preferably 0.2 MPa or less, and further preferably 0.11 MPa or less from the viewpoint of burden on facilities.

It is preferred that aging is performed after supplying the dialkyl sulfate to the alkanolamine ester in the step 2 from the viewpoint of reduction of the unreacted starting material to improve the reaction ratio. The aging temperature is preferably 30° C. or higher, more preferably 40° C. or higher, and further preferably 50° C. or higher from the viewpoint of improvement of the reaction rate, and is preferably 100° C. or lower, more preferably 90° C. or lower, further preferably 80° C. or lower, and furthermore preferably 70° C. or lower from the viewpoint of prevention of deterioration of smell and prevention of a side reaction. The aging time is preferably 0.5 hours or more, and more preferably 1 hour or more from the viewpoint of reduction of the unreacted starting material to improve the reaction ratio, and is preferably 20 hours or less, more preferably 10 hours or less, further preferably 5 hours or less, furthermore preferably 4 hours or less, and furthermore preferably 3 hours or less from the viewpoint of productivity.

The aging may be performed at normal pressure or may be performed under pressure or under reduced pressure. A preferred range of the pressure in the aging is the same as the preferred range of the pressure in the quaternization reaction described above.

In the step 2, from the viewpoint of stabilization of the hue, it is preferred to use a phenolic antioxidant. As the phenolic antioxidant, preferably one or more selected from a bis-alkylhydroxy toluene and a bis-alkylanisole, more preferably one or more selected from 2,6-di-tert-butyl-4-methylphenol (hereinafter, also referred to as "BHT") and 2,6-di-tert-butylanisole, further preferably BHT is used. The phenolic antioxidant to be used in the step 2 may be different from the phenolic antioxidant to be used in the step 1, but is preferably the same phenolic antioxidant as in the step 1 from the viewpoint of economic efficiency.

The using amount of the phenolic antioxidant with respect to 100 parts by mass of the alkanolamine ester obtained in the step 1 is preferably 0.005 parts by mass or more, more preferably 0.01 parts by mass or more, and further preferably 0.03 parts by mass or more from the viewpoint of stabilization of the hue, and is preferably 1.0 parts by mass or less, more preferably 0.5 parts by mass or less, and further preferably 0.3 parts by mass or less from the viewpoint of economic efficiency.

After completion of the quaternization in the step 2, in order to ensure the fluidity of the cationic surfactant by reducing the viscosity thereof, a solvent addition step can be performed as needed. The solvent addition step can be performed before or after the step 4 (which will be described later), but is preferably performed before the step 3 from the viewpoint of improvement of the operability.

As the solvent, any solvent can be used as long as it is a solvent which does not affect the quality even if it is used in a softener product. From the viewpoint of reduction of the viscosity of the cationic surfactant, the solvent is preferably an organic solvent, more preferably at least one organic solvent selected from alcohols having 2 or more and 3 or less carbon atoms and solvents represented by the above general formula (1), further preferably a monohydric alcohol having 2 or more and 3 or less carbon atoms or a polyhydric alcohol having 2 or more and 3 or less carbon atoms, and furthermore preferably ethanol or isopropyl alcohol. Further, from the viewpoint of the operability, in the case where the solvent is used in the step 2, the same solvent is preferably used.

The addition amount of the solvent in the cationic surfactant after adding the solvent is such that the sum of the addition amount thereof and the amount of the solvent used in the other steps is preferably 5% by mass or more, more preferably 8% by mass or more, and further preferably 10% by mass or more from the viewpoint of reduction of the viscosity to improve the handleability, and is preferably 60% by mass or less, more preferably 30% by mass or less, further preferably 20% by mass or less, and furthermore preferably 15% by mass or less from the viewpoint of economic efficiency.

The mixing temperature in the solvent addition step is preferably 30° C. or higher, more preferably 40° C. or higher, and further preferably 50° C. or higher from the viewpoint of enhancement of the ease of mixing and the mixing rate, and is preferably 90° C. or lower, more preferably 80° C. or lower, and further preferably 70° C. or lower from the viewpoint of reduction of deterioration of the quality such as color. Further, the mixing time is preferably 0.05 hours or more, and more preferably 0.1 hours or more from the viewpoint of uniformity of mixing, and is preferably 3 hours or less, more preferably 2 hours or less, and further preferably 1 hour or less from the viewpoint of productivity.

The step 3 of the present invention is a step of performing an oxidation treatment of the cationic surfactant obtained in the step 2. The oxidation treatment is performed from the viewpoint of prevention of deterioration of smell, and can be performed by, for example, oxygen oxidation using air as the atmospheric gas, or by mixing with a common oxidizing agent, or the like.

The oxidizing agent is preferably one or more selected from chlorous acid, hypochlorous acid, and alkali metal salts thereof, more preferably one or more selected from chlorous acid, hypochlorous acid, and sodium salts thereof, further preferably sodium chlorite or sodium hypochlorite, and furthermore preferably sodium chlorite from the viewpoint of prevention of deterioration of smell.

The using amount of the oxidizing agent with respect to 100 parts by mass of the cationic surfactant obtained in the step 2 is preferably 0.001 parts by mass or more, more preferably 0.005 parts by mass or more, further preferably 0.01 parts by mass or more, and furthermore preferably 0.03 parts by mass or more from the viewpoint of enhancement of the effect of preventing smelling, and is preferably 1.0 parts by mass or less, more preferably 0.5 parts by mass or less, further preferably 0.3 parts by mass or less, furthermore preferably 0.2 parts by mass or less, and furthermore preferably 0.1 parts by mass or less from the viewpoint of enhancement of the effect of preventing smelling and the viewpoint of prevention of deterioration of the hue.

The oxidizing agent is preferably used in the form of an aqueous solution from the viewpoint of handleability. The concentration of the oxidizing agent is preferably 10% by mass or more, and more preferably 20% by mass or more, and is preferably 50% by mass or less, more preferably 40% by mass or less, and further preferably 30% by mass or less from the viewpoint of availability and economic efficiency.

The temperature in the oxidation treatment is preferably 30° C. or higher, more preferably 40° C. or higher, and further preferably 50° C. or higher from the viewpoint of enhancement of the effect of preventing smelling, and is preferably 90° C. or lower, more preferably 80° C. or lower, and further preferably 70° C. or lower from the viewpoint of prevention of deterioration of the hue. The treatment time is preferably 0.05 hours or more, and more preferably 0.1 hours or more from the viewpoint of enhancement of the effect of preventing smelling, and is preferably 5 hours or less, and more preferably 2 hours or less from the viewpoint of productivity. In the case where the oxidation treatment is performed using an oxidizing agent, from the viewpoint of prevention of deterioration of the hue and the like, it is preferred to use an inert atmosphere, and from the viewpoint of economic efficiency, nitrogen gas is preferably used as the inert gas.

The step 4 of the present invention is a step of performing a reduction treatment of the cationic surfactant subjected to the oxidation treatment in the step 3. By sequentially performing the oxidation treatment and the reduction treatment after the quaternization in the step 2 in this manner, a high quality cationic surfactant, which is prevented from smelling and coloring, and also has favorable storage stability can be obtained.

The reduction treatment in the step 4 can be performed by mixing a reducing agent in the cationic surfactant. As the reducing agent, a common reducing agent can be used. From the viewpoint of prevention of deterioration of the hue to improve the storage stability, the reducing agent is preferably hypophosphoric acid or an alkali metal salt thereof, more preferably hypophosphoric acid or sodium hypophosphite, and further preferably hypophosphoric acid. The reduction treatment is preferably performed in an inert atmosphere from the viewpoint of prevention of deterioration of the quality such as color, and from the viewpoint of economic efficiency, nitrogen gas is preferably used as the inert gas.

The using amount of the reducing agent in the step 4 with respect to 100 parts by mass of the cationic surfactant obtained in the step 2 is preferably 0.001 parts by mass or more, more preferably 0.005 parts by mass or more, further preferably 0.01 parts by mass or more, furthermore preferably 0.02 parts by mass or more, and furthermore preferably 0.03 parts by mass or more from the viewpoint of prevention of deterioration of the hue to improve the storage stability, and is preferably 1.0 parts by mass or less, more preferably 0.5 parts by mass or less, further preferably 0.2 parts by mass or less, and furthermore preferably 0.1 parts by mass or less from the viewpoint of economic efficiency.

The reducing agent is preferably used in the form of an aqueous solution from the viewpoint of handleability. The concentration of the reducing agent is preferably 30% by mass or more, more preferably 40% by mass or more, and further preferably 45% by mass or more, and is preferably 70% by mass or less, more preferably 60% by mass or less, and further preferably 55% by mass or less from the viewpoint of availability and economic efficiency.

The temperature in the reduction treatment in the step 4 is preferably 30° C. or higher, more preferably 40° C. or higher, and further preferably 50° C. or higher from the viewpoint of prevention of deterioration of the hue to improve the storage stability, and is preferably 90° C. or lower, more preferably 80° C. or lower, and further preferably 70° C. or lower from the viewpoint of prevention of deterioration of the hue. The treatment time is preferably 0.05 hours or more, and more preferably 0.1 hours or more from the viewpoint of prevention of deterioration of the hue to improve the storage stability, and is preferably 5 hours or less, and more preferably 2 hours or less from the viewpoint of productivity.

The cationic surfactant obtained by the production method according to the present invention is prevented from smelling and coloring, and has favorable storage stability. The obtained cationic surfactant is useful as a softening base to be used in a fabric softener, and also has favorable biodegradability.

In the case where the cationic surfactant is used in a fabric softener composition as a softening base, the content of the cationic surfactant is preferably 1.0% by mass or more, more preferably 2.0% by mass or more, and further preferably 3.0% by mass or more from the viewpoint of appropriate exhibition of the softening performance, and is preferably 40% by mass or less, more preferably 30% by mass or less, and further preferably 20% by mass or less from the viewpoint of the sense of use and economic efficiency.

In order to further improve the softening performance and the storage stability, the fabric softener composition can contain a nonionic surfactant such as an alkylene oxide adduct of an alcohol having 8 or more and 24 or less carbon atoms, a higher alcohol such as an alcohol having 8 or more and 24 or less carbon atoms, a higher fatty acid such as a fatty acid having 8 or more and 24 or less carbon atoms, a lower alcohol such as ethanol or isopropanol, glycol, polyol, an ethylene oxide adduct thereof, a propylene oxide adduct thereof, or the like, and also can contain an inorganic salt, a pH adjusting agent, a hydrotropic agent, a fragrance, a defoamer, a pigment, or the like as needed.

Hereinafter, embodiments of the present invention will be listed.

<1>

A method for producing a cationic surfactant including the following step 1, step 2, step 3, and step 4:

step 1: a step of obtaining an alkanolamine ester by reacting an alkanolamine with a fatty acid or a fatty acid alkyl ester without using hypophosphoric acid or a salt thereof;

step 2: a step of obtaining a cationic surfactant by quaternizing the alkanolamine ester obtained in the step 1 with a dialkyl sulfate;

step 3: a step of performing an oxidation treatment of the cationic surfactant obtained in the step 2; and step 4: a step of performing a reduction treatment of the cationic surfactant subjected to the oxidation treatment obtained in the step 3.

<2>

The production method according to <1>, wherein the alkanolamine is preferably a dialkanolamine or a trialkanolamine, more preferably an aminoalcohol such as triethanolamine or methyldiethanolamine, further preferably triethanolamine.

<3>

The production method according to <1> or <2>, wherein the fatty acid is a long-chain fatty acid having preferably 8 or more and 30 or less carbon atoms, and more preferably 12 or more and 24 or less carbon atoms such as beef tallow fatty acid, hydrogenated beef tallow fatty acid, palm oil fatty acid, hydrogenated palm oil fatty acid, or a mixture of two or more members selected from these fatty acids, and the fatty acid alkyl ester is preferably a lower alkyl ester, more preferably a lower alkyl ester having 1 or more and 3 or less carbon atoms, and further preferably methyl ester of any of these fatty acids.

<4>

The production method according to any one of <1> to <3>, wherein the esterification degree of the alkanolamine ester is preferably 1.0 or more, more preferably 1.2 or more, further preferably 1.4 or more, and furthermore preferably 1.6 or more, and is preferably 2.2 or less, more preferably 2.0 or less, further preferably 1.8 or less, and furthermore preferably 1.7 or less.

<5>

The production method according to any one of <1> to <4>, wherein in the step 1, a carrier gas such as an inert gas, preferably nitrogen gas is used.

<6>

The production method according to any one of <1> to <5>, wherein the reaction temperature in the step 1 is preferably 140° C. or higher, and more preferably 160° C. or higher, and is preferably 230° C. or lower, more preferably 210° C. or lower, and further preferably 200° C. or lower.

<7>

The production method according to any one of <1> to <6>, wherein the reaction pressure in the step 1 is preferably a reduced pressure, more preferably 50 kPa or less, and further preferably 20 kPa or less, and is preferably 1 kPa or more, and more preferably 5 kPa or more.

<8>

The production method according to any one of <1> to <7>, wherein the reaction time in the step 1 is preferably 0.5 hours or more, more preferably 1 hour or more, further preferably 2 hours or more, furthermore preferably 3 hours or more, and furthermore preferably 6 hours or more, and is preferably 20 hours or less, more preferably 15 hours or less, further preferably 10 hours or less, and furthermore preferably 8 hours or less.

<9>

The production method according to any one of <1> to <8>, wherein the acid value (mgKOH/g) of the alkanolamine ester obtained in the step 1 is preferably 10 or less, more preferably 6 or less, further preferably 4 or less, furthermore preferably 3 or less, and furthermore preferably 2.5 or less, and is 0.5 or more, 1.0 or more, 1.5 or more, or 1.7 or more.

<10>

The production method according to any one of <1> to <9>, wherein the dialkyl sulfate to be used in the step 2 is preferably dimethyl sulfate or diethyl sulfate, and more preferably dimethyl sulfate.

<11>

The production method according to any one of <1> to <10>, wherein in the step 2, preferably a carrier gas such as an inert gas, more preferably nitrogen gas is used.

<12>

The production method according to any one of <1> to <11>, wherein the using amount of the dialkyl sulfate in the step 2 with respect to 1 equivalent of the alkanolamine ester is preferably 0.90 equivalents or more, and more preferably 0.93 equivalents or more, and is preferably 1.00 equivalent or less, and more preferably 0.98 equivalents or less.

<13>

The production method according to any one of <1> to <12>, wherein in the step 2, the quaternization reaction is preferably performed in the absence of solvents.

<14>

The production method according to any one of <1> to <12>, wherein the quaternization reaction is preferably a reaction which is performed while supplying the dialkyl sulfate to the alkanolamine ester.

<15>

The production method according to <14>, wherein the supply temperature of the dialkyl sulfate in the step 2 is preferably 30° C. or higher, and more preferably 40° C. or higher, and is preferably 100° C. or lower, more preferably 90° C. or lower, further preferably 80° C. or lower, and furthermore preferably 70° C. or lower.

<16>

The production method according to <14> or <15>, wherein the supply time of the dialkyl sulfate in the step 2 is preferably 0.1 hours or more, more preferably 0.25 hours or more, further preferably 0.5 hours or more, and furthermore preferably 1 hour or more, and is preferably 20 hours or less, more preferably 10 hours or less, further preferably 5 hours or less, furthermore preferably 4 hours or less, and furthermore preferably 3 hours or less.

<17>

The production method according to any one of <1> to <16>, wherein the pressure in the quaternization reaction in the step 2 is, in absolute pressure, preferably 0.09 MPa or more, and more preferably 0.10 MPa or more, and is preferably 0.5 MPa or less, more preferably 0.2 MPa or less, and further preferably 0.11 MPa or less.

<18>

The production method according to any one of <1> to <17>, wherein in the step 2, it is preferred to perform aging after supplying the dialkyl sulfate to the alkanolamine ester.

<19>

The production method according to <18>, wherein in the step 2, the aging step is performed at preferably 30° C. or higher, more preferably 40° C. or higher, and further preferably 50° C. or higher, and is preferably performed at 100° C. or lower, more preferably 90° C. or lower, further preferably 80° C. or lower, and furthermore preferably 70° C. or lower.

<20>

The production method according to any one of <18> and <19>, wherein in the step 2, the aging step is performed for preferably 0.5 hours or more, and more preferably 1 hour or more, and is performed for preferably 20 hours or less, more preferably 10 hours or less, further preferably 5 hours or less, furthermore preferably 4 hours or less, and furthermore preferably 3 hours or less.

<21>

The production method according to any one of <18> to <20>, wherein in the step 2, the aging step is performed at an absolute pressure of preferably 0.09 MPa or more, and more preferably 0.10 MPa or more, and is performed at an absolute pressure of preferably 0.5 MPa or less, more preferably 0.2 MPa or less, and further preferably 0.11 MPa or less.

<22>

The production method according to any one of <1> to <21>, wherein a solvent addition step is performed after completion of the quaternization in the step 2, and preferably performed before the step 3.

<23>

The production method according to <22>, wherein the solvent is preferably an organic solvent, more preferably at least one organic solvent selected from alcohols having 2 or more and 3 or less carbon atoms and solvents represented by the following general formula (1), further preferably a monohydric alcohol having 2 or more and 3 or less carbon atoms or a polyhydric alcohol having 2 or more and 3 or less carbon atoms, and furthermore preferably ethanol or isopropyl alcohol, and is also preferably the same solvent as used in the step 2.

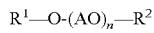  (1)

In the formula, $R^1$ and $R^2$ are the same or different and each represent hydrogen, an alkyl group having 1 or more and 30 or less carbon atoms, an alkenyl group having 1 or more and 30 or less carbon atoms, or an acyl group having 1 or more and 30 or less carbon atoms; A represents an alkylene group having 2 or more and 4 or less carbon atoms, and n represents a number on average of 1 or more and 40 or less, and A's are all the same or some of them are different.

<24>

The production method according to any one of <22> and <23>, wherein the addition amount of the solvent in the cationic surfactant after adding the solvent is such that the sum of the addition amount thereof and the amount of the solvent used in the other steps is preferably 5% by mass or more, more preferably 8% by mass or more, and further preferably 10% by mass or more, and is preferably 60% by mass or less, more preferably 30% by mass or less, further preferably 20% by mass or less, and furthermore preferably 15% by mass or less.

<25>

The production method according to any one of <22> to <24>, wherein the mixing temperature in the solvent addition step is preferably 30° C. or higher, more preferably 40° C. or higher, and further preferably 50° C. or higher, and is preferably 90° C. or lower, more preferably 80° C. or lower, and further preferably 70° C. or lower.

<26>

The production method according to any one of <22> to <25>, wherein the mixing time in the solvent addition step is preferably 0.05 hours or more, and more preferably 0.1 hours or more, and is preferably 3 hours or less, more preferably 2 hours or less, and further preferably 1 hour or less.

<27>

The production method according to any one of <1> to <26>, wherein the oxidation treatment in the step 3 is performed by oxygen oxidation of the cationic surfactant obtained in the step 2 or by mixing of an oxidizing agent, preferably performed by mixing of an oxidizing agent.

<28>

The production method according to <27>, wherein the oxidizing agent is preferably one or more selected from chlorous acid, hypochlorous acid, and alkali metal salts thereof, more preferably one or more selected from chlorous acid, hypochlorous acid, and sodium salts thereof, further preferably sodium chlorite or sodium hypochlorite, and furthermore preferably sodium chlorite.

<29>

The production method according to <27> or <28>, wherein the using amount of the oxidizing agent with respect to 100 parts by mass of the cationic surfactant obtained in the step 2 is preferably 0.001 parts by mass or more, more preferably 0.005 parts by mass or more, further preferably 0.01 parts by mass or more, and furthermore preferably 0.03 parts by mass or more, and is preferably 1.0 part by mass or less, further preferably 0.5 parts by mass or less, further preferably 0.3 parts by mass or less, furthermore preferably 0.2 parts by mass or less, and furthermore preferably 0.1 parts by mass or less.

<30>

The production method according to any one of <27> to <29>, wherein the oxidizing agent is preferably used in the form of an aqueous solution.

<31>

The production method according to <30>, wherein the concentration of the oxidizing agent is preferably 10% by mass or more, and more preferably 20% by mass or more, and is preferably 50% by mass or less, more preferably 40% by mass or less, and further preferably 30% by mass or less.

<32>

The production method according to anyone of <1> to <31>, wherein the temperature in the oxidation treatment is preferably 30° C. or higher, more preferably 40° C. or higher, and further preferably 50° C. or higher, and is preferably 90° C. or lower, more preferably 80° C. or lower, and further preferably 70° C. or lower.

<33>

The production method according to any one of <1> to <32>, wherein the oxidation treatment time is preferably 0.05 hours or more, and more preferably 0.1 hours or more, and is preferably 5 hours or less, and more preferably 2 hours or less.

<34>

The production method according to any one of <1> to <33>, wherein the step 3 is preferably performed in an inert atmosphere, and more preferably, nitrogen gas is used.

<35>

The production method according to any one of <1> to <34>, wherein the reduction treatment in the step 4 is a treatment in which the cationic surfactant subjected to the oxidation treatment in the step 3 and a reducing agent are mixed with each other.

<36>

The production method according to <35>, wherein the reducing agent is preferably hypophosphoric acid or an alkali metal salt thereof, more preferably hypophosphoric acid or sodium hypophosphite, and further preferably hypophosphoric acid.

<37>

The production method according to <35> or <36>, wherein the using amount of the reducing agent with respect to 100 parts by mass of the cationic surfactant obtained in the step 2 is preferably 0.001 parts by mass or more, more preferably 0.005 parts by mass or more, further preferably 0.01 parts by mass or more, furthermore preferably 0.02 parts by mass or more, and furthermore preferably 0.03 parts by mass or more, and is preferably 1.0 part by mass or less, more preferably 0.5 parts by mass or less, further preferably 0.2 parts by mass or less, and furthermore preferably 0.1 parts by mass or less.

<38>

The production method according to any one of <35> to <37>, wherein the reducing agent is preferably used in the form of an aqueous solution.

<39>

The production method according to <38>, wherein the concentration of the reducing agent is preferably 30% by mass or more, more preferably 40% by mass or more, and further preferably 45% by mass or more, and is preferably 70% by mass or less, more preferably 60% by mass or less, and further preferably 55% by mass or less.

<40>

The production method according to any one of <1> to <39>, wherein the temperature in the reduction treatment is preferably 30° C. or higher, more preferably 40° C. or higher, and further preferably 50° C. or higher, and is preferably 90° C. or lower, more preferably 80° C. or lower, and further preferably 70° C. or lower.

<41>

The production method according to any one of <1> to <40>, wherein the reduction treatment time is preferably 0.05 hours or more, and more preferably 0.1 hours or more, and is preferably 5 hours or less, and more preferably 2 hours or less.

<42>

The production method according to any one of <1> to <41>, wherein the step 4 is preferably performed in an inert atmosphere, and more preferably, nitrogen gas is used.

<43>

A cationic surfactant obtained by the production method according to any one of <1> to <42>.

<44>

The cationic surfactant according to <43>, which is used in a softening base of a fabric softener.

<45>

Use of the cationic surfactant according to <43> as a softening base of a fabric softener.

<46>

A fabric softener composition, containing the cationic surfactant according to <43> in an amount of preferably 1.0% by mass or more, more preferably 2.0% by mass or more, and further preferably 3.0% by mass or more, and preferably 40% by mass or less, more preferably 30% by mass or less, and further preferably 20% by mass or less.

EXAMPLES

The "%" in the examples is on a mass basis unless otherwise specified.

Example 1

As the step 1, in a 1 L reaction vessel, triethanolamine (1.0 mol, triethanolamine-S, manufactured by Nippon Shokubai Co., Ltd.), partially hydrogenated palm fatty acid (1.65 mol, Palmac 605T, manufactured by ACIDCHEM), and 0.28 g of BHT were placed, and the resulting mixture was purged with nitrogen. Then, while bubbling nitrogen, the internal pressure of the vessel was reduced at 170° C. from normal pressure (0.1 MPa) to 13.3 kPa over 1 hour, and then, an esterification reaction was performed for 7 hours, whereby 569 g of triethanolamine ester having an acid value of 2.0 mgKOH/g was obtained.

Subsequently, as the step 2, 512 g (0.9 mol) of the triethanolamine ester obtained in the step 1 and 0.7 g of BHT were mixed, and to the resulting mixture, 107.8 g (0.855 mol) of dimethyl sulfate was added dropwise over 2 hours at a temperature ranging from 45° C. to 65° C. in a nitrogen atmosphere at normal pressure (0.1 MPa). After performing aging at a temperature from 60° C. to 65° C. for 1.5 hours, 84.9 g of ethanol was added thereto so that the amount of the solvent in the final cationic surfactant became 12% by mass, followed by mixing at a temperature from 55° C. to 65° C. for 0.5 hours.

Further, as the step 3, 1.4 g of a 25% aqueous solution of sodium chlorite was added thereto, followed by mixing at a temperature from 55° C. to 65° C. for 0.5 hours, whereby an oxidation treatment was performed. Thereafter, as the step 4, 0.35 g of a 50% aqueous solution of hypophosphoric acid was added thereto, followed by mixing at a temperature from 55° C. to 65° C. for 0.5 hours, whereby a reduction treatment was performed, and thus, a cationic surfactant was obtained. Incidentally, in Table 1, the net contents (parts by mass) of the oxidizing agent and the reducing agent with respect to 100 parts by mass of the cationic surfactant are shown. With respect to the obtained cationic surfactant, the smell and color were evaluated by the following methods immediately after the cationic surfactant was produced and after the cationic surfactant was stored in a nitrogen atmosphere at 60° C. for 8 weeks. The results are shown in Table 1.

<Evaluation Sample for Smell and Evaluation Method>

Preparation was performed by placing 100 g of a 15% aqueous solution of the bulk substance in a 450 mL glass bottle.

Sensory evaluation was performed by 5 professional panelists according to the following criteria, and an average of the scores given by the panelists was determined as an evaluation value (a passing evaluation value for smell is 3.5 or less).

1: The sample has no offensive odor.
2: The sample has almost no offensive odor (has a very slight offensive odor).
3: The sample has a weak offensive odor.
4: The sample has a distinct offensive odor.
5: The sample has a strong offensive odor.
6: The sample has a very strong offensive odor.

<Evaluation for Color>

The color was measured according to the Gardner color scale using OME 2000 manufactured by Nippon Denshoku Industries Co., Ltd.

Example 2

A cationic surfactant was obtained by performing a procedure in the same manner as in Example 1 except that the amount of the 25% aqueous solution of sodium chlorite in the step 3 was changed to 4.2 g, and the amount of the 50% aqueous solution of hypophosphoric acid in the step 4 was changed to 0.71 g. The results obtained by performing the same evaluation as in Example 1 for the obtained cationic surfactant are shown in Table 1.

Example 3

A cationic surfactant was obtained by performing a procedure in the same manner as in Example 1 except that the amount of the 25% aqueous solution of sodium chlorite in the step 3 was changed to 0.56 g, and the amount of the 50% aqueous solution of hypophosphoric acid in the step 4 was changed to 0.71 g. The results obtained by performing the same evaluation as in Example 1 for the obtained cationic surfactant are shown in Table 1.

Example 4

A cationic surfactant was obtained by performing a procedure in the same manner as in Example 1 except that the amount of the 50% aqueous solution of hypophosphoric acid in the step 4 was changed to 0.71 g. The results obtained by performing the same evaluation as in Example 1 for the obtained cationic surfactant are shown in Table 1.

Example 5

A cationic surfactant was obtained by performing a procedure in the same manner as in Example 1 except that the amount of the 50% aqueous solution of hypophosphoric acid in the step 4 was changed to 0.14 g. The results obtained by performing the same evaluation as in Example 1 for the obtained cationic surfactant are shown in Table 1.

Example 6

A procedure was performed under the same conditions as in Example 1 except that nitrogen was bubbled in the step 1 at a flow rate shown in Table 1, and the internal pressure of the vessel was reduced at 190° C. from normal pressure (0.1 MPa) to 13.3 kPa over 1 hour, and then, an esterification reaction was performed for 4 hours, whereby 569 g of triethanolamine ester having an acid value of 2.1 mgKOH/g was obtained.

Subsequently, as the step 2, a procedure was performed in the same manner as in Example 1 except that aging was performed for 2.5 hours after dropwise addition of dimethyl sulfate, whereby a cationic surfactant was obtained. The results obtained by performing the same evaluation as in Example 1 for the obtained cationic surfactant are shown in Table 1.

Example 7

A cationic surfactant was obtained by performing a procedure in the same manner as in Example 1 except that the oxidizing agent in the step 3 was changed to sodium hypochlorite. The results obtained by performing the same evaluation as in Example 1 for the obtained cationic surfactant are shown in Table 1.

Comparative Example 1

A cationic surfactant was obtained by performing a procedure in the same manner as in Example 1 except that the step 3 and the step 4 were not performed. The results obtained by performing the same evaluation as in Example 1 for the obtained cationic surfactant are shown in Table 1.

Comparative Example 2

A cationic surfactant was obtained by performing a procedure in the same manner as in Example 1 except that the step 4 was not performed. The results obtained by performing the same evaluation as in Example 1 for the obtained cationic surfactant are shown in Table 1.

Comparative Example 3

A cationic surfactant was obtained by performing a procedure in the same manner as in Example 1 except that the step 3 was not performed. The results obtained by performing the same evaluation as in Example 1 for the obtained cationic surfactant are shown in Table 1.

Comparative Example 4

A cationic surfactant was obtained by performing a procedure in the same manner as in Example 1 except that the order of the treatments in the step 3 and the step 4 performed in Example 1 was changed. The results obtained by performing the same evaluation as in Example 1 for the obtained cationic surfactant are shown in Table 1.

Comparative Example 5

A cationic surfactant was obtained by performing a procedure in the same manner as in Example 1 except that in the step 1, 0.57 g of a 50% aqueous solution of hypophosphoric acid (a net content of 0.05 parts by mass with respect to 100 parts by mass of triethanolamine ester) was added, and dehydration esterification was performed for 3 hours as the aging, whereby 569 g of triethanolamine ester having an acid value of 1.6 mgKOH/g was obtained. The results obtained by performing the same evaluation as in Example 1 for the obtained cationic surfactant are shown in Table 1.

TABLE 1

|  |  | Example 1 | Example 2 | Example 3 | Example 4 | Example 5 | Example 6 |
|---|---|---|---|---|---|---|---|
| Step 1 | Hypophosphoric acid [parts by mass]*1 | — | The same as in Example 1 | | | | — |
|  | Triethanolamine (g) | 149 | | | | | 149 |
|  | Fatty acid (g) | 449 | | | | | 449 |
|  | Fatty acid/triethanolamine [eq/eq] | 1.65 | | | | | 1.65 |
|  | Reaction temperature [° C.] | 170 | | | | | 190 |
|  | Reaction pressure [kPa] | 13.3 | | | | | 13.3 |
|  | Reaction time [hr] | 7 | | | | | 4 |
|  | Carrier gas | Nitrogen bubbling 50 mL/min | | | | | Nitrogen bubbling 10 mL/min |
| Step 2 | Dimethyl sulfate [eq] | 0.95 | The same as in Example 1 | | | | 0.95 |
|  | Dimethyl sulfate supply temperature (° C.) | 45-65 | | | | | 45-65 |
|  | Dimethyl sulfate supply time (° C.) | 2.0 | | | | | 2.0 |
|  | Aging temperature [° C.] | 60-65 | | | | | 60-65 |
|  | Aging time [hr] | 1.5 | | | | | 2.5 |
| Step 3 | Oxidation treatment | NaClO₂ 0.05 parts by mass 55-65° C./0.5 h | NaClO₂ 0.15 parts by mass 55-65° C./0.5 h | NaClO₂ 0.02 parts by mass 55-65° C./0.5 h | NaClO₂ 0.05 parts by mass 55-65° C./0.5 h | NaClO₂ 0.05 parts by mass 55-65° C./0.5 h | NaClO₂ 0.05 parts by mass 55-65° C./0.5 h |
| Step 4 | Reduction treatment | Hypophosphoric acid 0.025 parts by mass 55-65° C./0.5 h | Hypophosphoric acid 0.05 parts by mass 55-65° C./0.5 h | Hypophosphoric acid 0.05 parts by mass 55-65° C./0.5 h | Hypophosphoric acid 0.05 parts by mass 55-65° C./0.5 h | Hypophosphoric acid 0.01 parts by mass 55-65° C./0.5 h | Hypophosphoric acid 0.025 parts by mass 55-65° C./0.5 h |

TABLE 1-continued

| | | | | | | | |
|---|---|---|---|---|---|---|---|
| Common to Steps 2 to 4 | Atmospheric gas | Nitrogen | Nitrogen | Nitrogen | Nitrogen | Nitrogen | Nitrogen |
| Evaluation of product | Immediately after production | Smell | 1.0 | 1.2 | 1.2 | 1.0 | 1.0 | 1.2 |
| | | Color [G] | 1 | 1 | 1 | 1 | 1 | 1 |
| | After storage at 60° C. for 8 weeks | Smell | 2.0 | 1.8 | 2.2 | 1.8 | 2.0 | 2.2 |
| | | Color [G] | 2 | 2 | 2 | 2 | 3 | 2 |

| | | | Example 7 | Comparative Example 1 | Comparative Example 2 | Comparative Example 3 | Comparative Example 4 | Comparative Example 5 |
|---|---|---|---|---|---|---|---|---|
| Step 1 | Hypophosphoric acid [parts by mass]*¹ | | The same as in Example 1 | The same as in Example 1 | | | | 0.05 |
| | Triethanolamine (g) | | | | | | | 149 |
| | Fatty acid (g) | | | | | | | 449 |
| | Fatty acid/triethanolamine [eq/eq] | | | | | | | 1.65 |
| | Reaction temperature [° C.] | | | | | | | 170 |
| | Reaction pressure [kPa] | | | | | | | 13.3 |
| | Reaction time [hr] | | | | | | | 3 |
| | Carrier gas | | | | | | | Nitrogen bubbling 50 mL/min |
| Step 2 | Dimethyl sulfate [eq] | | The same as in Example 1 | The same as in Example 1 | | | | The same as in Example 1 |
| | Dimethyl sulfate supply temperature (° C.) | | | | | | | |
| | Dimethyl sulfate supply time (° C.) | | | | | | | |
| | Aging temperature [° C.] | | | | | | | |
| | Aging time [hr] | | | | | | | |
| Step 3 | Oxidation treatment | | NaClO 0.05 parts by mass 55-65° C./0.5 h | Non | NaClO₂ 0.05 parts by mass 55-65° C./0.5 h | Non | Hypophosphoric acid 0.025 parts by mass 55-65° C./0.5 h | NaClO₂ 0.05 parts by mass 55-65° C./0.5 h |
| Step 4 | Reduction treatment | | Hypo-phosphoric acid 0.025 parts by mass 55-65° C./0.5 h | Non | Non | Hypo-phosphoric acid 0.025 parts by mass 55-65° C./0.5 h | NaClO₂ 0.05 parts by mass 55-65° C./0.5 h | Hypo-phosphoric acid 0.025 parts by Mass 55-65° C./0.5 h |
| Common to Steps 2 to 4 | Atmospheric gas | | Nitrogen | Nitrogen | Nitrogen | Nitrogen | Nitrogen | Nitrogen |
| Evaluation of product | Immediately after production | Smell | 1.4 | 1.0 | 1.0 | 5.8 | 4.0 | 4.4 |
| | | Color [G] | 1 | 1 | 1 | 1 | 1 | 1 |
| | After storage at 60° C. for 8 weeks | Smell | 2.4 | 3.8 | 3.0 | 6.0 | 5.0 | 5.4 |
| | | Color [G] | 2.5 | 6 | 6 | 2.5 | 2 | 2.5 |

*¹parts by mass with respect to 100 parts by mass of the total amount of the alkanolamine, the fatty acid, and the fatty acid alkyl ester in Step 1

The invention claimed is:

1. A method for producing a cationic surfactant comprising the following step 1, step 2, step 3, and step 4:
   step 1: a step of obtaining an alkanolamine ester by reacting an alkanolamine with a fatty acid or a fatty acid alkyl ester without using hypophosphoric acid or a salt thereof;
   step 2: a step of obtaining a cationic surfactant by quaternizing the alkanolamine ester obtained in the step 1 with a dialkyl sulfate;
   step 3: a step of performing an oxidation treatment of the cationic surfactant obtained in the step 2; and
   step 4: a step of performing a reduction treatment of the cationic surfactant subjected to the oxidation treatment obtained in the step 3.

2. The method for producing a cationic surfactant according to claim 1, wherein the oxidation treatment in the step 3 is a treatment in which the cationic surfactant and an oxidizing agent are mixed with each other, and the using amount of the oxidizing agent is 0.001 parts by mass or more and 1.0 parts by mass or less with respect to 100 parts by mass of the cationic surfactant obtained in the step 2.

3. The method for producing a cationic surfactant according to claim 2, wherein the oxidizing agent is one or more selected from chlorous acid, hypochlorous acid, and alkali metal salts thereof.

4. The method for producing a cationic surfactant according to claim 1, wherein the reduction treatment in the step 4 is a treatment in which the cationic surfactant and a reducing agent are mixed with each other, the reducing agent is hypophosphoric acid or an alkali metal salt thereof, and the using amount of the reducing agent is 0.001 parts by mass or more and 1.0 parts by mass or less with respect to 100 parts by mass of the cationic surfactant obtained in the step 2.

5. The method for producing a cationic surfactant according to claim 1, wherein the alkanolamine is a dialkanolamine or a trialkanolamine.

6. The method for producing a cationic surfactant according to claim 1, wherein the alkanolamine is methyldiethanolamine or triethanolamine.

7. The method for producing a cationic surfactant according to claim 1, wherein in the step 2, the quaternization reaction is performed in the absence of solvents.

8. The method for producing a cationic surfactant according to claim 1, wherein after completion of the quaternization in the step 2, a solvent addition step is performed before the step 3.

9. The method for producing a cationic surfactant according to claim 8, wherein the solvent is at least one organic solvent selected from alcohols having 2 or more and 3 or less carbon atoms and solvents represented by the following general formula (1):

$$R^1\text{—O-}(AO)_n\text{—}R^2 \qquad (1)$$

wherein $R^1$ and $R^2$ are the same or different and each represent hydrogen, an alkyl group having 1 or more and 30 or less carbon atoms, an alkenyl group having 1 or more and 30 or less carbon atoms, or an acyl group having 1 or more and 30 or less carbon atoms; A represents an alkylene group having 2 or more and 4 or less carbon atoms, and n represents a number on average of 1 or more and 40 or less, and A's are all the same or some of them are different.

10. The method for producing a cationic surfactant according to claim 8, wherein the addition amount of the solvent in the cationic surfactant after adding the solvent is such that the sum of the addition amount thereof and the amount of the solvent used in the other steps is 5% by mass or more and 60% by mass or less.

11. The method for producing a cationic surfactant according to claim 2, wherein the oxidizing agent is used in the form of an aqueous solution.

12. The method for producing a cationic surfactant according to claim 1, wherein the temperature in the oxidation treatment is 30° C. or higher and 90° C. or lower.

13. The method for producing a cationic surfactant according to claim 4, wherein the reducing agent is used in the form of an aqueous solution.

14. The method for producing a cationic surfactant according claim 1, wherein the temperature in the reduction treatment is 30° C. or higher and 90° C. or lower.

* * * * *